United States Patent [19]

Sutor

[11] Patent Number: 5,648,124
[45] Date of Patent: Jul. 15, 1997

[54] PROCESS FOR PREPARING MAGNETICALLY RESPONSIVE MICROPARTICLES

[75] Inventor: James J. Sutor, Indianapolis, Ind.

[73] Assignee: Seradyn, Inc., Indianapolis, Ind.

[21] Appl. No.: 447,050

[22] Filed: May 22, 1995

Related U.S. Application Data

[63] Continuation-in-part of Ser. No. 87,862, Jul. 9, 1993, abandoned.

[51] Int. Cl.$^6$ ........................................ B05D 1/04
[52] U.S. Cl. .................. 427/475; 427/129; 427/130; 427/131; 427/190; 427/203; 427/205; 427/213.33; 427/213.36; 427/214; 427/222; 427/322; 427/385.5; 427/412.1; 427/419.2; 427/430.1
[58] Field of Search ..................... 427/212, 214, 427/215, 221, 475, 129, 130, 131, 190, 203, 205, 213.33, 213.36, 222, 322, 385.5, 412.1, 419.2, 430.1

[56] References Cited

U.S. PATENT DOCUMENTS

| 4,695,392 | 9/1987 | Whitehead et al. | 252/62.54 |
| 5,091,206 | 2/1992 | Wang et al. | 427/2 |

Primary Examiner—Bernard Pianalto
Attorney, Agent, or Firm—Oblon, Spivak, McClelland, Maier & Neustadt, P.C.

[57] ABSTRACT

Magnetically responsive microparticles and a method for their production are described. Oppositely charged core particles and magnetite are heterocoagulated, redispersed and optionally coated. The microparticles are colloidally stable and have negligible retentivity.

Having now fully described the invention, it will be apparent to one of ordinary skill in the art that many changes and modifications can be made thereto without departing from the spirit or scope of the invention as set forth herein.

17 Claims, 1 Drawing Sheet

PROCESS FOR PREPARING MAGNETICALLY RESPONSIVE MICROPARTICLES

This application is a continuation in part application of U.S. application Ser. No. 08/087,862, filed Jul. 9, 1993 now abandoned, incorporated herein by reference.

BACKGROUND OF THE INVENTION

Field of the INvention

Magnetically responsive microparticles are useful in biological techniques requiring the separation of bound from free fractions. Magnetically responsive particles useful in immunoassays, for the separation of cells, as magnetic resonance imaging agents, etc. have been described in U.S. Pat. Nos. 4,770,183, 4,695,392, 4,329,241, 4,230,685, 4,177,253, 5,069,216, and 5,091,206, all incorporated herein by reference.

Preferably, magnetically responsive microparticles have negligible residual magnetism, and when used in immunoassays, preferably have diameters which cover the range of the visible light spectrum so as to facilitate heterogeneous and homogeneous immunoassay methods.

Unfortunately, prior art magnetically responsive microparticles have considerable residual magnetism due to the greater than single domain size of the magnetic materials utilized. Such residual magnetism causes clumping in the absence of a magnetic field causing the magnetic particles to fall out of Brownian motion and settle out of suspension quickly. Further, the large size of the prior art aggregates of magnetite used in magnetically responsive microparticles limits the overall size of the microparticle. For example, U.S. Pat. No. 5,091,206 provides 1 micron polymer cores coated with approximately 600–800 nm diameter particles of a magnetic metal oxide. Thus, the overall size of the particles is at least approximately 2.2 microns.

SUMMARY OF THE INVENTION

Accordingly, one object of this invention is to provide a novel method for producing magnetically responsive microparticles having negligible residual magnetism.

Another object of the present invention is to provide a magnetically responsive microparticle whose magnetite content can be varied.

Another object of the present invention is the production of a magnetically responsive microparticle having a coating of magnetite particles which are subdomain in size and which exhibits negligible residual magnetism.

Another object of the present invention is the production of a magnetically responsive microparticle whose overall diameter can be varied within wide limits and which can cover the wavelength range of the visible light spectrum.

Another object of the present invention is the development of a magnetically responsive microparticle whose surface charge chemistry, hydrophobicity, etc., may be varied depending on the end use of the microparticle.

Another object of the present invention is the development of a magnetically responsive microparticle having a high surface area and negligible settling rate ideally suited for oligonucleotide synthesis, biological separations, immunoassays, etc.

Another object of the present invention is to provide magnetically responsive microparticles having more EMU's per gram of material than known microparticles.

Another object of the present invention is to provide microparticles which do not, in a PCR assay, activate or turnover the peroxidase substrate system to give false positive results.

Another object of the present invention is to provide a method of producing stable microparticles wherein magnetically responsive material is coagulated on a sphere, overcoated with polyethyleneimine (PEI) and crosslinked with polyacrylate, polymethacrylate, etc. The PEI can first be crosslinked. The particle so made is also an object herein Another object of the present invention is to provide magnetically responsive microparticles having polydespersity factors $\mu_2/\gamma^2$ preferably of from 0.003–0.300 including all values and all ranges therebetween.

Various other objects, features and attendant advantages of the present invention will be more fully appreciated as the same becomes better understood from the following detailed description when considered in connection with the accompanying drawing.

BRIEF DESCRIPTION OF THE DRAWING

The FIGURE is a cross sectional view of a magnetically responsive microparticle according to the present invention comprising an inner core (1), a coating of magnetically responsive material (2) and a polymeric outer shell (3).

DETAILED DESCRIPTION OF THE PREFERRED EMBODIMENTS

Figure 1:
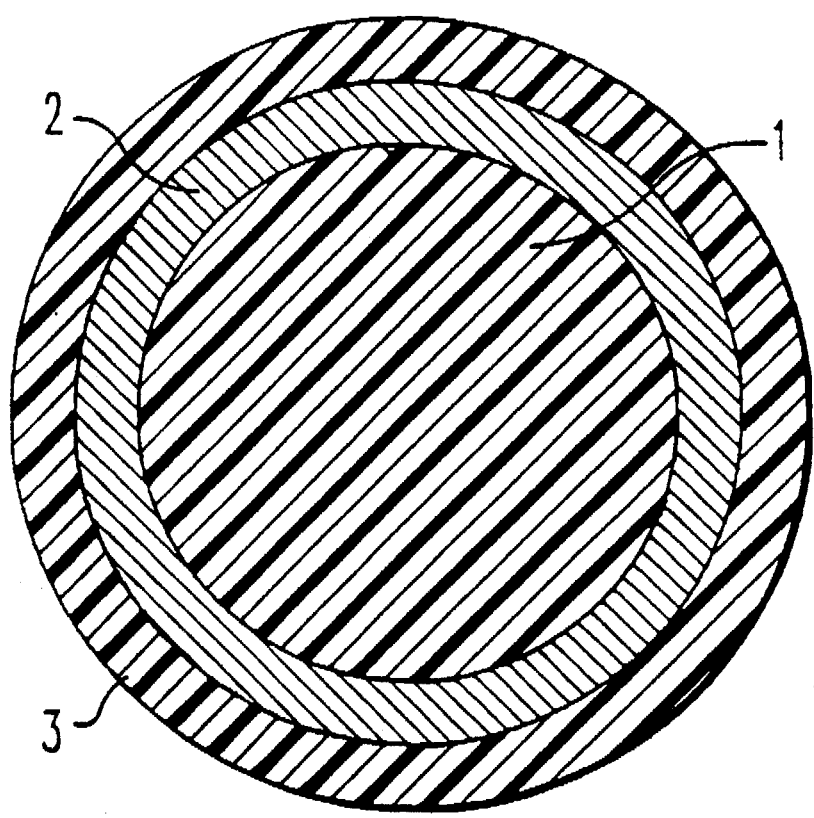

The magnetically responsive microparticles of the present invention are prepared by heterocoagulating colloidally stable aqueous dispersions of magnetically responsive material including ferrofluids, super ferrofluids, etc., such as paramagnetic or, preferably, superparamagnetic magnetite onto the surface of core particles. The cores and the magnetite are oppositely charged and heterocoagulate initially due to electrostatic attraction, and heterocoagulate further upon the addition of heterocoagulant. After the desired degree of heterocoagulation has been accomplished a polymeric dispersant is added which disperses the heterocoagulated magnetite-coated microparticles so as to suspend them in solution where they remain in Brownian motion in the absence of a magnetic field. If desired, the dispersed magnetite-coated microparticles may be crosslinked and/or further coated with one or more outer polymeric coatings.

The core particle of the invention may be made of any material including silica, alumina, albumin, polymers, etc., and be of any size and shape, but are preferably polymeric, spherical, monodisperse (i.e., have polydispersities of $\leq 0.1$ $\mu_2/\gamma^2$) and from 0.05 to 10.0 microns in size more preferably from 0.25 to 5.0 microns, and most preferably from 0.1 to 1.0 microns in size. Particularly useful sizes of core particles are 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 1.0, 1.1, 1.2, 1.3, 1.4, 1.5, 1.6, 1.7, 1.8, 1.9, and 2.0 microns. Polymeric core particles according to the invention may be obtained by any technique known in the art, with emulsion polymerization, seeded emulsion polymerization, and suspension polymerization being particularly preferred. The polymeric core particles may be made with or without a crosslinking agent. The core particles according to the invention are preferably non-magnetic.

Useful core particles include those made from styrene, methylstyrene, ethylstyrene, and homologs thereof, and methyl acrylate, ethyl acrylate, methyl methacrylate, ethyl methacrylate, and homologs thereof. The core particles may be prepared with or without the addition of ionogenic comonomers such as 2-acrylamido-2-methyl propanesulfonic acid (AMPS), sodium allyl sulfonate, sodium methallyl sulfonate, vinyl sulfonate, sodium p-styrene sulfonate, potassium p-styrene sulfonate, acrylic acid, fumaric acid, maleic acid, methacrylic acid, itaconic acid, and salts thereof; aminoethylmethacylate, dimethylaminoethyl methacrylate, t-butylaminoethyl methacrylate, pyrrole, N-vinyl carbazole, vinylpyridines, and salts thereof. Of course a mixture of the monomers and optional comonomers may be used to produce polymeric cores having the desired size and surface charge characteristics. Particularly preferred polymeric cores are those of polymethylmethacrylate, carboxylate-modified polymethylmethacrylate, polystyrene, and carboxylate-modified polystyrene.

The surface of the polymeric cores of the present invention may be prepared with positive or negative charge. For example, if the core is made with polyacrylic acid, the acid groups will impart a negative charge to the surface of the core. If the core is made with aminoethylmethacrylate, the amino groups will impart a positive charge to the surface of the core. For polymers having no active hydrogens (e.g., polystyrene), surface charge may be provided by the initiator used to produce the polymer. For example, styrene monomer polymerized in the presence of a persulfate initiator will provide a polystyrene core having a negative surface charge while polystyrene polymerized with 2,2'-azobis (2-methylpropionamidine)dihydrochloride initiator will provide polystyrene with a positive charge. Examples of initiators which provide a negative charge are persulfate, 4,4'-azobis (4-cyanovaleric acid) and potassium peroxydiphosphate. Any initiator that provides a negative surface charge may be used. Any initiator which provides a positive charge may be used. The surface charge of the core particle is measured by conductiometric titration and is generally from 0.005 to 1.5, preferably 0.01 to 1.0, milliequivalents per gram of core particle.

The superparamagnetic magnetite of the present invention may be prepared by the addition of base to an aqueous mixture of ferrous and ferric sulfate or chloride. A mixture of $FeCl_3$ and $FeCl_2$ is preferred. A preferred base is ammonium hydroxide. The molar ratio of the trivalent to the divalent metal salt can be varied form 1.0-3.0, preferable from 1.8 to 2.2, to obtain the desired size and magnetic characteristics of the superparamagnetic material. Divalent transitional metal salts such as cadmium, cobalt, copper, magnesium, manganese, nickel, zinc salts and their mixtures, may be substituted for some or all of the ferrous salt. Other superparamagnetic particles according to the present invention, and methods for their preparation, are described in U.S. Pat. No. 4,810,401, incorporated herein by reference.

The magnetically responsive material including the superparamagnetic magnetite according to the present invention is preferably peptized or finely divided, to subdomain size such that no net magnetic dipole remains in the individual grains of magnetite. Typically, the size of the peptized aggregates varies from 0.1 to 200 nm as measured by quasielastic light scattering, is preferably from 1 to 120 nm, more preferably from 30 to 70 nm. Peptized aggregates of 10, 20, 30, 40, 50, 60, 70, 80, 90, 100, 110, and 120 nm are particularly useful in the invention. Peptizing may by accomplished by treating the coarse aggregates of magnetite with acid or base until the desired size is obtained. Further, a net positive or negative surface charge is imparted to the invention superparamegnetic magnetite by the acid or base. Since magnetite is amphoteric, treatment with acid produces a positively charged superparamagnetic magnetite, and treatment with base produces a negatively charged superparamagnetic magnetite.

The superferrofluids which may be used in the present invention as magnetically responsive material to coat the above-described cores include mixed $CO_yMn_wZn_xFe_yO_4$ and $Ni_zMn_wZn_xFe_yO_4$ and others described in U.S. Pat. No. 4,810,401 incorporated herein by reference. Particularly preferred superferrofluids have magnetic saturations of up to 40% greater than magnetite ($Fe_3O_4$) including all values and all ranges therebetween. $CO_{0.1}Mn_{0.2}Zn_{0.2}Fe_{2.5}O_{3.7}$ and $Ni_{0.1}Mn_{0.2}Zn_{0.2}Fe_{2.5}O_{3.96}$ are particularly preferred.

The magnetic saturation of a magnetically responsive material according to the invention has been found to be process dependent. For example, a process is described in Example 8 herein where a magnetite ferrofluid has a saturation of 73.7 emu/gm. If the superferrofluid materials described above were used in the same process, the saturation would be from 5–40% greater depending on the specific material.

The heterocoagulant of the present invention, also referred to herein as a binding agent, includes, alone or in combination, ammonium or alkali metal salts of sulfate and phosphate; free radical generating ammonium or alkali metal salts of peroxydisulfate, peroxydiphosphate, and 4,4-azobis (4-cyanovaleric acid); ammonium or alkali metal salts of oxalic acid, malonic acid, succinic acid, glutaric acid, etc.; polymerizable ammonium or alkali metal salts of fumaric acid, maleic acid, and itaconic acid; ammonium or alkali metal salts of alkyl sulfonates such as dihexylsulfosuccinate and dioctylsulfosuccinate; polymerizable ammonium or alkali metal salts of alpha olefin sulfonates, alkyl allyl sulfosuccinates, and allyl ether sulfonate, the latter three surfactants having 6 to 30 carbon atoms; ammonia, alkylamines, and polyalkylamines such as polyethylenimine; polyacrylic acid and water soluble copolymers and salts thereof, polymethacrylic acid and water soluble copolymers and salts thereof, polystyrenesulfonic acid and water soluble copolymers and salts thereof, polyvinylsulfonic acid and water soluble copolymers and salts thereof, styrene/maleic acid copolymers, half esters, and salts thereof, vinyl methyl ether/maleic acid copolymers, half esters, and salts thereof, all with weight average molecular weights of 1,000 to 100,000. The ammonium or alkali metal sulfates and phosphates may be generated in situ by the thermal decomposition of homogeneous precipitating agents such as dimethyl sulfate, sulfamic acid, or trimethyl phosphate if so desired. Ammonia may be generated in situ by the thermal decomposition of urea. The heterocoagulants are solid or liquid at room temperature and are generally used in amounts of from 0.01 to 0.20 grams per gram of core particles being coated with magnetite. Preferred hetercoagulants are ammonium sulfate, sodium dioctylsulfosuccinate, polyacrylic acid, and polymethacrylic acid.

The polymeric dispersants of the present invention include, alone or in combination, polyacrylic acid and water soluble copolymers and salts thereof, polymethacrylic acid and water soluble copolymers and salts thereof, polystyrenesulfonic acid and water soluble copolymers and salts thereof, polyvinylsulfonic acid and water soluble copolymers and salts thereof, styrene/maleic acid copolymers, half esters, and salts thereof, vinyl methyl ether/maleic acid copolymers, half esters, and salts thereof, and polyethyleneimine all preferably, but not necessarily, with weight average molecular weights of 1,000 to 100,000. The polymeric dispersant may also serve as the heterocoagulant. Polyacrylic acid, polyethyleneimine, polymethacrylic acid and their combinations are preferred. The polymeric dispersant is preferably is added as a solution at room temperature; however, powdered polymeric dispersant may be used as well. The most preferred dispersant is polyethyleneimine.

The amount of polymeric dispersant added varies from 0.05 to 0.20 grams per gram of core particles being coated with magnetite. Other preferred polymeric dispersants and their approximate molecular weight are polyacrylic acid MW (weight average)=2,000 to 100,000 and polymethacrylic acid MW (weight average)=2,000 to 100,000.

According to the invention, magnetically responsive microparticles are made by preparing an aqueous dispersion of oppositely charged magnetically responsive material (MRM) and core particles. Since the MRM and the core particles have opposite net charges, heterocoagulation (i.e., the coming together) of the MRM and the core particles occurs in the absence of the heterocoagulant until the core is coated with approximately one layer of the magnetite particles. Upon addition of the heterocoagulant to the aqueous dispersion of charged MRM and oppositely charge core particles, further heterocoagulation takes place: the MRM further coats the core particles. Accordingly, since heterocoagulation occurs upon the addition of the hetercoagulant, the amount of MRM coated onto the microparticles may be controlled such that the total weight of the magnetically responsive heterocoagulated microparticles is 0.1 to 80 wt %, preferably 10–50 wt % magnetite. Using cores with diameters of 0.1 to 10 microns and magnetite with a particle sizes of 30 to 70 nm, magnetically responsive microparticles having overall diameters of 0.16 to 12, preferably 0.3 to 5 microns, more preferably 0.8 to 1.2 microns, may be produced. Useful overall diameters of the invention magnetically responsive microparticles are 0.005, 0.01, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0 and 2.1 microns.

Of course, the order of addition of core particles, MRM and hetercoagulant may be varied. For example, core particles and hetercoagulant may be prepared in an aqueous dispersion and MRM added thereto. Alternatively, MRM and core particles may be prepared in an aqueous dispersion and the hetercoagulant added thereto, or the three materials may be added to water singly in any order. Heterocoagulation preferably takes place at room temperature but is effective at temperatures ranging form 0° to 100° C. Any known method for mixing the components may be used.

As heterocoagulation proceeds, the magnetically responsive microparticles tend to flocculate, forming large easily visible aggregates. Addition of the polymeric dispersant to this slurry redisperses the magnetically responsive microparticles and places them back into Brownian motion. The addition of the polymeric dispersant may be carried out at room temperature or at a temperature of from 0° to 100° C., optionally with stirring. Any know method for preparing aqueous dispersions may be used. The amount of dispersant added is the amount necessary to place the magnetically responsive microparticles into Brownian motion.

After the magnetically responsive microparticles have been redispersed, the core/MRM/heterocoagulant/dispersant particle may be directly overcoated with, e.g., styrene (see below). Optionally, any carboxylic acid groups of the dispersant may be further cross-linked by any number of means known in the art e.g., to facilitate overcoating. Crosslinking may be accomplished with homobifunctional $C_4$–$C_{17}$ amines, aziridines, and epoxides, or with epichlorohydrin.

A particularly preferred surface is one prepared by crosslinking the polymeric dispersant (e.g., polyacrylic acid) on the magnetite-coated core particle with hexanediamine (HDA). Any percentage of crosslinking, preferably 10, 20, 30, 40, 50, 60, 70, 80, 90, or 100%, more preferably 80 to 100% of the total crosslinkable groups of the polymeric dispersant may be cross linked. Coupling agents like 1-ethyl-3-(3-dimethylaminopropyl)carbodiimide (EDC) or chloroethylformate may be used to effect crosslinking at room temperature.

Crosslinking with excess hexanediamine yields an amino-modified microparticle. Any free amine (e.g., HDA bonded to only one carboxyl) may be converted back to a terminal carboxyl with succinic anhydride, if so desired.

The polyamide or nylon-like coating made of carboxyl groups cross linked with hexanediamine (HDA) described above can be further overcoated with, e.g., styrene (see Saito, R. Eur. Polym. J. Vol 27, No. 10, pp 1153–1159, 1991, incorporated herein by reference), as explained below.

The outer polymeric coating optionally overcoated on the core/MRM/heterocoagulant/dispersant (or cross-linked dispersant) microparticle may be applied directly by adding the polymeric coating itself or the desired coating monomer (s) and a polymerization initiator to the suspended, dispersed microparticles followed by heating, irradiation with light, exposure to gamma radiation, etc. in order to initiate polymerization of the monomers. The outer polymeric coating may be crosslinked, if desired.

Preferred monomers useful for preparing the outer polymeric coating include acidic monomers such as acrylic acid, methacrylic acidfumaric acid, maleic acid, methacrylic acid, itaconic acid, vinyl acetic acid, 4-pentenoic acid, undecylenic acid, and salts thereof; basic monomers such as aminoethylmethacylate, dimethylaminoethyl methacrylate, t-butylaminoethyl methacrylate, pyrrole, N-vinyl carbazole, vinylpyridine, and salts thereof; hydrophobic neutral monomers such as methyl acrylate, ethyl acrylate, methyl methacrylate, ethyl methacrylate, styrene, methylstyrene, ethylstyrene, vinylnaphthalene, and homologs thereof. If a polymer is added in polymerized form as the overcoating copolymers and polymers of the above monomers can be used. Preferred polymerization initiators include benzoyl peroxide, lauryl peroxide, 4,4-azobis (4-cyanovaleric acid), azoisobutyronitrile (AIBN) and potassium persulfate. Preferred crosslinking agents include allyl methacrylate, divinylbenzene, and ethylene glycol dimethacrylate. Of course, mixtures of monomers, initiators, and crosslinking agents may be used.

The amount of monomer added in order to form an outer polymeric coating generally depends upon the amount of magnetite heterocoagulated on the core particle. Generally, the amount used varies between 0.2 and 1.0 grams of monomer (or polymer if that is used) per gram of non-coated core particle.

Another preferred outer polymeric coating is made by first neutralizing an acidic polymeric dispersant on the magnetite-coated core particle with a basic monomer like dimethylaminoethyl methylmethacrylate and then polymerizing with styrene. See U.S. Pat. No. 3,965,284 incorporated herein by reference. Template polymerization results when the polymeric dispersant used is polymethylacrylic acid and is neutralized with N-vinylcarbazole (see van de Grample, H. T., Macromol. Chem. Macromol. Symp. 1988, 20/21, 83, incorporated herein by reference). The outermost polymeric coating described above can itself be cross-linked with HDA, homobifunctional amines, etc., as described above.

These several outer coating strategies address the problem of encapsulating a hydrophilic amphoteric core surface surrounded by a hydrophilic protective colloid with uncharged hydrophobic monomers. Unsatisfactory overcoating results in magnetic microparticles that literally come apart upon exposure to acid or base solution which makes the net charge on the magnetite reverse. The overall sizes of the invention magnetically responsive microparticles mentioned above include the outer polymeric coating.

In one preferred aspect of the present invention, MRM is heterocoagulated onto a microparticle as above, polyethyleneimine (PEI) being used as a dispersant, as above and even as the heterocoagulant, if desired. The PEI can then be crosslinked with itself. Useful crosslinkers here are ethylene dibromide, ethylenedichloride, ethylene glycol diacrylate, formaldehyde, gluteraldehyde, hexamethylene diisocyanate, N',N-methylenebisacrylamide, methylenebisexposide, and any other suitable bifunctional, preferably hom, obifunctional crosslinking agent. The PEI coating (crosslinked or not) can be over-coated with polyacrylic acid (PAA), polymethacrylic acid (PMAA), or both, followed by the crosslinking of PEI with the PAA and/or PMAA using, e.g., one or more of 1-ethyl-2-(3-dimethylaminopropyl) carbodiimide (EDAC), N'N'-dicyclohexylcarbodiimide, ethylchloroformate, etc. The PAA and/or PMAA could be further treated as described above to provide, e.g., a nylon surface, etc. and even further overcoated with, e.g., styrene.

Not wanting to be limited to any particular theory, it is believed that the process of the present invention, since it relies upon heterocoagulation, guarantees that the magnetic dipoles of the aggregates of magnetite remain unaligned as they are absorbed randomly onto the surface of the core particle, even at high magnetite loadings. Accordingly, the magnetically responsive microparticles prepared according to the invention exhibit negligible residual magnetism having magnetic squareness of less than 0.1 and remain in suspension for long periods of time. The magnetic squareness of the invention microparticles varies between 0, 0.005, 0.01, 0.02, 0.025, 0.03, 0.04, 0.05, 0.06, 0.07, 0.08, 0.09 and 0.1. Magnetic squareness is defined as rententivity divided by magnetism. Squareness is a measure of the residual magnetism left in the microparticles after being exposed to a magnetic field. A magnetic squareness of 0.1 means that 10% of the induced magnetism remains. A magnetic squareness of 0.02 means that only 2% of the induced magnetism remains.

The magnetically responsive microparticles according to the present invention are best characterized by their behavior when suspended in water. In particular, magnetically responsive microparticles according to the invention are colloidally stable in water and exhibit zero to negligible residual magnetism. The term colloidally stable as used herein means that microparticles according to the present invention, when dispersed in water at concentrations from 0.1 to 10 grams per 100 cc may be seen to be in brownian motion, fully dispersed, and not clumped together when a 10 microliter sample of the dispersion under a cover slip is examined at 400× magnification using an inverted light microscope. The magnetic microparticles according to the invention may also be sized by quasielastic light scattering (QELS). Particles that are not colloidally stable can not be sized by QELS.

Colloidally stable microparticles according to the invention, when dispersed in water at a total solids loading of 5 to 10 grams per 100 cc, show ≦25% settling after approximately one month of sitting undisturbed at room temperature. The settling amount is measured by determining that portion of the total volume which is clear and which does not contain dispersed microparticles after initial dispersion of the particles in 100% of the total volume.

The microparticles of the present invention also have negligible hysteresis, where negligible includes no hysteresis. Hysteresis is the measure of residual magnetism in a magnetic microparticle once a microparticle has been exposed to a magnet and the magnet has been pulled away. Magnetic microparticles according to the invention having negligible to no hysteresis and/or the magnetic squareness values mentioned above are easily redispersed by gentle stirring, vortexing, shaking, etc. Particles that exhibit negligible hysteresis typically have magnetic squareness values of <0.1.

As described above, the magnetic particles according to the invention may be used in immunoassays, etc. wherein an antigen or antibody is bound to the coated particles. Such bonding may be accomplished by physical adsorption or by covalent chemical bonding with, e.g., carbodiimide. Such antigen/antibody functionalization is known in the art and described in, e.g., E.P. 420,186, incorporated herein by reference. In particular, strepavadin has been coupled to magnetic particles produced according to the above-described process and the activity of the bound strepavadin was confirmed using a functional assay.

Having generally described this invention, a further understanding can be obtained by reference to certain specific examples which are provided herein for purposes of illustration only and are not intended to be limiting unless otherwise specified.

Preparation of Ferrofluids

EXAMPLE 1

A solution of 112.8 gms of FeCl3.6H2O in 100 mls of deoxygenated water and a solution of 41.2 gms of FeCl2.4H2O in 100 mls of deoxygenated water were prepared. The ferrous and ferric chloride salt solutions were added to 800 mls of deoxygenated water under argon.

The mixed salt solution was chilled to approximately 6° C. 200 mls of 28 wt % ammonium hydroxide was then added slowly with stirring while maintaining the reaction temperature below 6° C. The resulting black slurry of mixed ferrous and ferric hydroxides was heated to 90° C. for 30 minutes under argon.

The slurry thus formed was cooled to room temperature, magnetically decanted and resuspended in 800 mls of deionized water. The slurry was stirred with a mechanical stirrer for 5 minutes, magnetically decanted and resuspended in 500 mls of deionized water. The washed slurry was peptized by adding 112 mls of 60 wt % perchloric acid and stirring for 10 minutes, magnetically decanted and resuspended in 500 mls of deionized water. The slurry was peptized a second time by adding 81 mls of 60 wt % perchloric acid and stirring for 10 minutes, magnetically decanted and resuspended in 500 mls of deionized water.

The peptized slurry was poured into 6000–8000 MW cutoff dialysis tubing and dialyzed continuously against deionized water overnight. The dialyzed slurry was magnetically decanted for two hours. The ferrofluid was carefully poured off and filtered through Whatman #6 paper.

Yield: 600.8 gms ferrofluid @4.2 wt % Fe3O4 (52.3% of theory) having an average particle size of approximately 95 nm.

EXAMPLE 2

A solution of 112.8 gms of FeCl3.6H2O in 100 mls of deoxygenated water and a solution of 41.2 gms of FeCl2.H$_2$O in 100 mls of deoxygenated water were prepared. The ferrous and ferric chloride salt solutions were added to 800 mls of deoxygenated water under argon.

The mixed salt solution was chilled to 6° C. 200 mls of 28 wt % ammonium hydroxide was then added slowly with stirring while still maintaining the reaction temperature below 6° C. The resulting black slurry of mixed ferrous and ferric hydroxides was first heated to 37° C. at which point 23.37 gms of glycine dissolved in 100 mls of deoxygenated deionized water was added. The solution was then heated to 90° C. for 30 minutes under argon.

The slurry thus formed was cooled to room temperature, magnetically decanted and resuspended in 800 mls of deionized water. The slurry was stirred for 5 minutes, magnetically decanted and resuspended in 500 mls of deionized water. The washed slurry was peptized by adding 112 mls of 60% perchloric acid and stirring with a mechanical stirrer for 10 minutes, magnetically decanted and resuspended in 500 mls of deionized water. The slurry was peptized a second time by adding 81 mls of 60% perchloric acid and stirring for 10 minutes, magnetically decanted and resuspended in 500 mls of deionized water.

The peptide slurry was poured into 6000–8000 MW cutoff dialysis tubing and dialyzed continuously against deionized water overnight. The dialyzed slurry was magnetically decanted for two hours. The ferrofluid was carefully poured off and filtered through Whatman #6 paper.

Yield: 556.6 gms ferrofluid @ 5.6 wt % (64.7% of theory) with an average particle size of approximately 45 nm.
Preparation of a Core Particle by Seeded Emulsion

EXAMPLE 3

To a 1000 ml 3-neck round bottom flask fitted with a condenser and mechanical stirrer was charged 169.6 gms of a 0.503 micron diameter monodispersed polystyrene microsphere seed suspension 350.5 gms purified water, 0.4502 gms potassium persulfate, and 0.4629 gms sodium bicarbonate. The buffered suspension of seed was purged with argon for 10 minutes then heated to 70° C. Once at temperature, 180.1 gms of styrene was added and the resulting polymerization allowed to proceed for 8 hours.

Yield: 669.0 gms of a 32.0% by weight suspension of 0.803 micron core microparticles.

EXAMPLE 4

Preparation of Magnetic Microparticles 156.3 gms of 6.4% colloidally stable positively charged ferrofluid with an average particle size of 57 nm was charged to a 110 volt Waring blender. 88.5 gms of a colloidally stable ion-exchanged cleaned 11.3% solids suspension of negatively charged microparticles (0.802 micrometer diameter, carboxylate modified polystyrene, parking area of 79.9 $A^2$/COOH group) was added while blending at 40% line voltage. The mixture was blended at 70% line voltage for 5 minutes. 10.0 mls of a 2.0% solids solution of Aerosol OT 75 (a sodium dialkylsulfosuccinate) was added dropwise while blending at 70% line voltage. 1.0 gms of polyacrylic acid MW=2000 was added. The mixture was then blended at 70% line voltage for 5 minutes.

The mixture was magnetically decanted overnight. A clear supernatant was siphoned off and the microparticles were resuspended in an equal volume of deionized water.

154.2 gms of the magnetic microparticle suspension at 7.28% solids containing 3.70 milliequivalents of carboxyl groups by condutiometric titration was obtained and 0.1722 gms, 2.96 milliequivalents of 1,6-hexanediamine dissolved in 10 mls of deionized water was added dropwise thereto with stirring followed by the addition of 1.776 gms, 9.26 milliequivalents, of EDC dissolved in 10 mls of deionized water. The suspension was stirred for 16 hours.

The magnetic microparticles were washed once in 200 mls deionized water by centrifugation and then resuspended in 200 mls of 50 Mm sodium phosphate buffer @ Ph 7.0.

Yield: 220.0 gms net @ 6.2% solids, 0.963 micron diameter by QELS.

The retentivity of the particles was 0.36 EMU/gm of suspension and the magnetization was 18.00 EMU/gm of suspension. The squareness was 0.02. The parking area (P) refers to the area in $Å^2$ surrounding each titratable carboxyl group and is calculated as follows:

$$P=1/S$$

where $$S=Dc \cdot d \cdot 1.004$$

and

S=surface charge density [charge groups $Å^2$]
Dc=charge density (meq/gr)
Ps=polymer bulk density
d=particle diameter
P=parking area

EXAMPLE 5

59.5 gms of 4.2 wt % colloidally stable positively changed ferrofluid having a particle size of 95 nm and 40.5 gms of deionized water was charged to a 1 liter 3-neck round bottom flask fitted with a mechanical stirrer. 100.0 gms of a colloidally stable 10.2 wt % solids suspension of negatively charged microparticles having a 0.924 micrometer diameter made from carboxylated modified polystyrene and having a parking area of 33.7$A^2$/COOH group was added while stirring. Heterocoagulation occurred and was indicated by a clear colorless supernate on exposure of a 1000 microliter sample to a magnetic field. 1.0 gm of polymethyacrylic acid (average molecular weight of 40,000–60,000) was added to the heterocoagulated mixture and the mixture was then stirred vigorously for 5 minutes. The heterocoagulated mixture of ferrofluid and carboxylate modified polystyrene microparticles redispersed. Each microparticle was magnetically responsive, having been evenly coated with a layer superparamagnetic magnetite.

2.5 gms of a 20:1:1 wt/wt/wt mixture of styrene, divinylbenzene 55 (divinylbenzene is available commercially at 55% purity and 80% purity, the balance is diethylbenzenes and other impurities) and lauroyl peroxide was added to 201.9 gms of the magnetically responsive microparticle suspension with stirring under argon. The suspension was stirred for 5 minutes and then heated to 70° C. for 15 hours while still under argon.

Yield: 189.0 gms net @ 5.5 wt % solids with a diameter of 0.970 by QELS. A suspension of these particles in water was colloidally stable and showed negligible retentivity and a squareness of 0.022.

EXAMPLE 6

51.0 gms of 4.9 wt % colloidally stable ferrofluid having a diameter of 0.45 nm and 49.0 gms of deionized water was charged to a 110 volt Waring blender. 98.0 gms of a colloidally stable 10.2 wt % solids suspension of microparticles (0.924 micrometer diameter,carboxylate modified polystyrene, parking area of 33.7 A²/COOH group) was added while blending at 40% line voltage for 5 minutes. 7.8 mls of a 12.8 wt % solids solution of ammonia-neutralized styrene-maleic anhydride resin (average molecular weight of 1000) was added dropwise as heterocoagulant while blending at 40% line voltage. The mixture heterocoagulated and was then blended at 100% line voltage for 5 minutes. The heterocoagulated mixture of ferrofluid and carboxylate modified polystyrene microparticles redispersed. Each microparticle was magnetically responsive having been evenly coated with a layer superparamagnetic magnetite.

1.0 gms of a 38:2:1 mix of styrene, divinylbenzene 55, and benzoyl peroxide was added to 182.7 gms net of the magnetically responsive microparticle suspension with stirring under argon. The suspension was stirred for one hour until all the monomer had been imbibed, and heated to 70° C. for 17 hours while still under argon to effect polymerization.

Yield: 172.2 gms net @ 5.8 wt % solids with a diameter of 0.978 by QELS. A suspension of these particles in water was colloidally stable and showed negligible retentivity and a squareness of 0.035.

EXAMPLE 7

Preparation of core microparticles.

To a 1000 ml 3-neck round bottom flask fitted with a condenser and mechanical stirrer was charged 169.0 gms monodispersed polystyrene microsphere suspension, 350.0 gms purified water, 0.4502 gms potassium persulfate, and 0.4629 gms sodium bicarbonate. The buffered suspension of seed was purged with argon for 10 minutes then heated to 70 degrees C. Once at temperature, 180.1 gms of styrene was added and the resulting polymerization allowed to proceed for 8 hours.

Yield: 669.0 gms of a 32% suspension of 0.803 micron core microparticles.

EXAMPLE 8

Preparation of $Fe_3O_4$ Ferrofluid

To 1500 mls of deionized water in a 4 liter beaker was added 54.7 gms (0.275 moles) of Iron(II) chloride tetrahydrate and 1.4.2 gms (0.386 moles) of Iron(II) chloride hexahydrate. The beaker was covered with parafilm and the salts stirred until dissolved. The resulting iron salt solution was then chilled to less than 10 degrees C. in an Ice bath with stirring.

To 900 mls of deionized water in a 1.5 liter beaker was added 223.9 gms of concentrated ammonium hydroxide (58%). The dilute ammonium hydroxide was then chilled to less than 10 degrees C. The dilute ammonium hydroxide was then pumped into the iron salt solution at 180 cc/min. The Ice bath is removed and the resulting black slurry stirred while sparging with air for 24 hours.

The slurry was magnetically decanted on an Eriez 175 mm×250 mm table top magnet, resuspended in 400 mls of deionized water, then adjusted to a pH of 1.4 with concentrated hydrochloric acid. After stirring three and a half hours, the peptized slurry was poured into 6000–8000 MW cutoff dialysis tubing and continously dialyzed against running deionized water overnight. The resulting ferrofluid was pooled and placed on the table top magnet for two hours to remove aggregates then carefully poured off and filtered through Whatman #6 paper.

Yield: 650.6 gms ferrofluid at 5.19% solids containing 4.55% iron as Fe3O4. The ferrofluid was a magnetic saturation of 73.7 emu/gm Fe3O4 by vibrating magnetometer.

EXAMPLE 9

Preparation of Glycine Stabilized $Fe_3O_4$ Ferrofluid

A solution of 112.8 gms (0.417) of Iron(III) chloride hexahydrate in 100 mls of deoxygenated water and a solution of 41.2 gms (0.207 moles) of Iron(II) chloride tetrahydrate in 100 mls of deoxygenated water was prepared. The ferrous and ferric chloride salt solutions was added to 800 mls of deoxygenated water under argon.

The mixed salt solution was chilled to less than 6 degrees C. 200 mls of 28% ammonium hydroxide was then added slowly with stirring while still maintaining the reaction temperature below 6 degrees C. The resulting black slurry of mixed ferrous and ferric hydroxides was first heated to 37 degrees C. at which point 23.37 gms of glycine dissolved in 100 mls of deoxygenated deionized water was added. The solution was then heated to 90 degrees for 30 minutes under argon.

The slurry thus formed was cooled to room temperature, magnetically decanted and resuspended in 800 mls of deionized water. The slurry was stirred for 5 minutes, magnetically decanted and resuspended in 500 mls of deionized water. The washed slurry was peptized by adding 112 mls of 60% perchloric acid and stirring for 10 minutes, magnetically decanted and resuspended in 500 mls of deionized water. The slurry was peptized a second time by adding 81 mls of 60% perchloric acid and stirring for 10 minutes, magnetically decanted and resuspended in 500 mls of deionized water.

The peptized slurry was poured into 6000–8000 MW cutoff dialysis tubing and dialyzed continuously against a deionized water overnight. The dialyzed slurry is magnetically decanted for two hours. The ferrofluid is carefully poured off and filtered through Whatman #6 paper.

Yield: 556.6 gms ferrofluid at 5.6% Fe3O4 (64.7% of theory).

EXAMPLE 10

Preparation of polyacrylic acid PAA Coated Magnetic Microparticles

To a 1 liter Waring blender was added 50 cc of 5.0% ferrofluid (2.5 gms solids) and 50 cc of deionized water to cover the blades. The blender was turned on low, then 92 cc of 10.8% ion-exchanged 0.967 µm carboxylate modified polystyrene particles (9.9 gms solids) were added slowly. The mixture is blended on high for five minutes then 10 cc of 1% PAA (average M.W. of 90,000) was added. On blending an additional 5 minutes on high, the particles were monodispersed when examined at 400× using an inverted light microscope.

Yield: 168.5 gms of PAA coated microparticles at 5.64% solids. The diameter by QELS is 1.050 µm with a polydispersity factor, $\mu_2/\gamma^2$, of 0.012.

EXAMPLE 11

Preparation of SMA Coated Magnetic Microparticles

To a 1 liter Waring blender was added 51 gms of 4.9% ferrofluid (2.5 gms solids) and 51 gms of deionized water. The mixture was blended on high for 5 minutes then 98 gms of 10.2% uncleaned 0.927 µm carboxylate modified polystyrene particles (10.0 gms solids) were added. The mixture was blended on high for another 5 minutes then 7.8 mls of ammonia neutralized SMA 1000 (styrene-maleic anhydride) resin (1 gm) was added dropwise. On blending the mixture on high for an additional 5 minutes the particles were monodispersed when examined at 400× using an inverted light microscope.

Yield: 182.7 gms of SMA coated microparticles

EXAMPLE 12

Preparation of PMAA polymethycrylic acid Coated Magnetic Microparticles

To a 1 liter Waring blender was added 59.5 gms of 4.2% ferrofluid (2.5 gms solids) and 40.5 gms of deionized water. Blended the mixture at 40% line voltage while adding 98 gms of 10.2% uncleaned 0.927 μm carboxylate modified polystyrene (10.0 gms solids). 1.0048 gms of powdered PMAA was added then blended at 80% line voltage for 5 minutes. The particles were monodispersed when examined at 400× using an inverted light microscope.

Yield: 187.4 gms of PMAA coated microparticles at 5.5% solids. The pH of the dispersion is 4.1.

EXAMPLE 13

Preparation of polyehtyleneimine PEI Coated Magnetic Microparticles

To a 4 liter Waring blender (model CB6) was added 549.0 gms of 5.2% ferrofluid (28.5 gms solids) and 192.0 gms of 10% ion-exchanged cleaned 0.806 μm carboxylate modified polystyrene microparticles (20.0 gms solids). The mixture was blended at low speed for one minute then 200 mls of 2M NaCl was added at 180 cc/min. while blending. The mixture was blended for another minute at low speed then 100 mls of 0.22 μm filtered 10% (w/w) PEI (average M.W. of 50,000–60,000) was added at 180 cc/min. while blending. Finally, the mixture was blended for another minute at low speed then magnetically decanted and resuspended four times in 1 liter of 0.25M NaCl.

Yield: 1249.5 gms of PEI coated microparticles at 5.12% solids.

EXAMPLE 14

Preparation of PEI/DAXAD 34/Glutaraldehyde Crosslinked Magnetic Microparticles

To a 400 ml beaker was added 54.9 gms of 6.63% ferrofluid (3.64 gms solids), 19.2 gms of 9.47% ion-exchanged cleaned 0.806 μm carboxylate modified polystyrene microparticles (1.82 gms solids), and 15.9 gms of deionized water. The mixture was sonicated at 30% output for 60 seconds using a Cole-Parmer model CP600 ultrasonic homogenizer fitted with a standard horn. 10 mls of 2.5M NaCl was added dropwise while sonicating. The mixture was sonicated for another minute at 30% output then 10 mls of 0.22 μm filtered 10% (w/w) PEI (average M.W. of 50,000–60,000) was added dropwise while sonicating. The mixture was magnetically decanted and resuspended four times in 100 mls of 0.25 m NaCl.

10 mls of 10% DAXAD 34 (polymethacrylic acid resin) was added dropwise while sonicating then the particles were magnetically decanted and resuspended three times in 100 of 0.25M NaCl then once in 50 m MMES buffer, pH 6.1. The particles were treated with 2.5% glutaraldehyde followed by another washing with MES buffer.

The microparticles may be further treated with EDAC to crosslink the PMAA to the PEI.

EXAMPLE 15

Preparation of PEI/DAXAD 34 Crosslinked Magnetic Microparticles

To a 4 liter Waring blender (model CB6) was added 549.0 gms of 5.2% ferrofluid (28.5 gms solids) and 192.0 gms of 10% ion-exchanged cleaned 0.806 μm carboxylate modified polystyrene microparticles (20.0 gms solids). The mixture was blended at low speed for one minute then 200 mls of 2M NaCl was added at 180 cc/min. while blending. The mixture was blended for another minute at low speed then 100 mls of 0.22 μm filtered 10% (w/w) PEI (average M.W. of 50,000–60,000) was added at 180 cc/min. while blending. Finally, the mixture was blended for another minute at low speed then magnetically decanted and resuspended four times in 1 liter of 0.25M NaCl.

The PEI coated magnetic microparticles were charged back to the blender and blended for one minute on low. 100 mls of 10% DAXAD 34 was added at 180 cc/min. while blending. The mixture was blended for another minute at low speed then magnetically decanted and resuspended three times in 1 liter of 0.25M NaCl, once in 1 liter of 50 mMMES buffer, pH 6.1, then stirred for 30 minutes.

25 gms of EDAC in 100 mls of deionized water was added to crosslink the coacervate. After 64 hours, the particles were washed twice with deionized water.

Yield: 811.8 gms at 5.00% solids. The diameter by QELS was 0.905 μm with a polydispersity factor, $\mu_2/\gamma^2$, of 0.267. The iron content as $Fe_3O_4$ is 46.76%.

The microparticles may be further treated with glutaraldehyde or other hetero- or homobifunctional crosslinking agents.

EXAMPLE 16

Preparation of $MnFe_2O_4$ Ferrofluid

To 500 mls of deionized water in a 4 liter beaker is added 39.6 gms (0.20 moles) of Manganese(II) chloride tetrahydrate and 108.1 gms (0.40 moles) of Iron(III) chloride hexahydrate. The salts are stirred until dissolved. The resulting Fe(III)-Mn(II) solution is heated to 100 degrees C. with stirring.

To 500 mls of deionized water in a 1 liter beaker is added 96 gms of NaOH pellets. The pellets are stirred till dissolved. The resulting caustic solution is heated to 100 degrees C. with stirring.

The caustic solution is then quickly poured into the Fe(III)-Mn(II) solution with vigorous stirring. The resulting brownish-black slurry is held at 100 degrees C. for one hour.

On cooling, the slurry is worked up as in Example 8.

EXAMPLE 17

Preparation of Ferric Nitrate Treated $MnFe_2O_4$ Ferrofluid

To 500 mls of deionized water in a 4 liter beaker is added 39.6 gms (0.20 moles) of Manganese(II) chloride tetrahydrate and 108.1 gms (0.40 moles) of Iron(III) chloride hexahydrate. The salts are stirred until dissolved. The resulting Fe(III)-Mn(II) solution is heated to 100 degrees C. with stirring.

To 500 mls of deionized after in a 1 liter beaker is added 96 gms of NaOH pellets. The pellets are stirred till dissolved. The resulting caustic solution is heated to 100 degrees C. with stirring.

The caustic solution is then quickly poured into the Fe(III)-Mn(II) solution with vigorous stirring. The resulting brownish-black slurry is held at 100 degrees C. for one hour then cooled.

The slurry is washed with 1 liter aliquots of 2N nitric acid till chloride free, resuspended in 1 liter of 0.1 molar iron(III) nitrate, then reheated to 100 degrees C. for one hour.

On cooling the slurry is worked up an in Example 2.

Having now fully described the invention, it will be apparent apparent to one of ordinary skill in the art that many changes and modifications can be made thereto without departing from the spirit or scope of the invention as set forth herein.

What is claimed as new and desired to be secured by Letters Patent of the United States is:

1. A method for the preparation of microparticles which are responsive to a magnetic field comprising the steps of:

1) providing an aqueous dispersion comprising electrically charged material which is responsive to a magnetic field and electrically charged core particles wherein said electrically charged material and electrically charged core particles are oppositely charged; and allowing said material and said core particles to heterocoagulate;

2) optionally adding a heterocoagulant to said dispersion obtained in 1) to effect further heterocoagulation of the core particles and the material;

3) adding a polymeric dispersant to the heterocoagulated core particles and material obtained in 1) or 2) so as to provide dispersed microparticles which are responsive to a magnetic field;

4) optionally crosslinking the polymeric dispersant on the microparticles produced in 3);

5) optionally coating the dispersed microparticles obtained in 3) or 4) with at least one coating polymer or with at least one polymerizable monomer and at least one polymerization initiator, followed by polymerization of said monomer.

2. The method as claimed in claim 1, comprising steps 1), 2), 3) and 5).

3. The method of claim 1, wherein said core comprises polystyrene.

4. The method of claim 1 wherein said material is particulate magnetite having a particle size of 1 to 120 nm.

5. The method of claim 4 wherein said particulate magnetite has a particle size of 30 to 70 nm.

6. The method of claim 1 wherein said microparticle has an overall diameter of from 0.2 to 2.0 microns.

7. The method of claim 6, wherein the overall diameter of the microparticle is 0.3–0.8 microns.

8. The method as claimed in claim 1, comprising steps 1), 3), 4) and 5).

9. The method of claim 1, wherein said polymeric dispersant comprises polyethyleneimine.

10. The method of claim 1, wherein said polymeric dispersant in step 3 is polyethyleneimine, and wherein said process comprises step 5, the coating polymer being polyacrylic acid and/or polymethacrylic acid.

11. The method of claim 10, wherein polyacrylic acid is used in step 5.

12. The method of claim 1, wherein the magnetic squareness of the microparticles is $\leq 0.05$.

13. The method as claimed in claim 1, wherein said polymeric dispersant comprises polyethyleneimine.

14. The method as claimed in claim 1, comprising steps 1), 2), and 3).

15. The method as claimed in claim 1, comprising steps 1)–4).

16. The method as claimed in claim 1, comprising steps 1)–5).

17. The method as claimed in claim 16, wherein said microparticles obtained in 4) are coated with a coating polymer, and wherein said coating polymer in step 5) is polyacrylic acid.

* * * * *